United States Patent [19]

Kaufman

[11] Patent Number: 5,198,349

[45] Date of Patent: Mar. 30, 1993

[54] METHOD FOR PRODUCING FACTOR VIII:C AND ANALOGS

[75] Inventor: Randal J. Kaufman, Boston, Mass.

[73] Assignee: Genetics Institute, Inc., Cambridge, Mass.

[21] Appl. No.: 707,211

[22] Filed: May 23, 1991

Related U.S. Application Data

[63] Continuation of Ser. No. 942,338, Dec. 16, 1986, abandoned, which a continuation-in-part of Ser. No. 816,031, Jan. 3, 1986, abandoned.

[51] Int. Cl.⁵ ............... C12P 21/02; C12N 15/10; C12N 5/16; C12N 15/85
[52] U.S. Cl. ............... 435/69.6; 435/69.1; 435/172.3; 435/240.2; 435/240.31; 435/320.1; 435/948; 530/383; 530/381; 530/380; 935/11; 935/70; 935/10; 935/60; 930/100
[58] Field of Search ............... 435/69.1, 172.3, 240.2, 435/240.31, 320.1, 948; 935/11, 70, 10, 60

[56] References Cited

U.S. PATENT DOCUMENTS

| Re. 32,011 | 10/1985 | Zimmerman et al. | 530/383 |
|---|---|---|---|
| 4,657,894 | 4/1987 | Zimmerman et al. | 514/21 |
| 4,670,394 | 6/1987 | Pollard et al. | 435/948 |
| 4,740,461 | 4/1988 | Kaufman | 435/69.6 |
| 4,749,780 | 6/1988 | Anderson et al. | 530/383 |
| 4,757,006 | 7/1988 | Toole et al. | 435/69.6 |

FOREIGN PATENT DOCUMENTS

| 0112174 | 6/1984 | European Pat. Off. | 435/240.31 |
|---|---|---|---|
| 0150735 | 8/1985 | European Pat. Off. | |
| 0157556 | 10/1985 | European Pat. Off. | |
| 0160457 | 11/1985 | European Pat. Off. | |
| 0169562 | 1/1986 | European Pat. Off. | |
| 0197592 | 10/1986 | European Pat. Off. | |
| 0232112 | 8/1987 | European Pat. Off. | |
| 0251843 | 1/1988 | European Pat. Off. | |
| 0253455 | 1/1988 | European Pat. Off. | |
| 0254076 | 1/1988 | European Pat. Off. | |
| 0255206 | 2/1988 | European Pat. Off. | |
| 0265778 | 5/1988 | European Pat. Off. | |
| 0013389 | 1/1983 | Japan | 435/240.3 |
| 0023784 | 2/1983 | Japan | 435/240.31 |
| 8501961 | 5/1985 | PCT Int'l Appl. | 435/240.2 |
| 8606096 | 10/1986 | World Int. Prop. O. | |
| 8606101 | 10/1986 | World Int. Prop. O. | |
| 8606745 | 11/1986 | World Int. Prop. O. | |
| 8704187 | 7/1987 | World Int. Prop. O. | |
| 8707144 | 12/1987 | World Int. Prop. O. | |
| 8800210 | 1/1988 | World Int. Prop. O. | |
| 8800831 | 2/1988 | World Int. Prop. O. | |
| 8803558 | 5/1988 | World Int. Prop. O. | |
| 8805825 | 8/1988 | World Int. Prop. O. | |

OTHER PUBLICATIONS

Kaufman et al. 1985. Molec. Cell. Biol. 5, 1750-1759.
Jakoby et al. (eds) 1979. in: Meth. Enzymol. vol. LVIII, pp. 88-90. Academic PRess.
Ginsburg et al. 1985. Science 228, 1401-1406.
Poake, I. R. 1984. Clin. Sci. 67, 561-567.
Kruse et al. (eds) 1973. In: Tissue Culture. Methods and Applications. Academic Press. New York. pp. 677-682.
Freshney, R. I. 1983. in:Culture of Animal Cells. A manual of Basic Technique Alan R. Liss, Inc., New York. pp. 67-78.
Weiss et al, Journal of Clinical Investigation 60 pp. 390-404 (1977).

(List continued on next page.)

Primary Examiner—Robert A. Wax
Assistant Examiner—Christopher S. F. Low
Attorney, Agent, or Firm—Maureen C. Meinert; Thomas J. DesRosier; Bruce Eisen

[57] ABSTRACT

An improved method for producing Factor VIII:c is disclosed. The method involves culturing mammalian cells which contain DNA encoding Factor VIII:c and which are capable of expressing Factor VIII:c. In accordance with this invention the cells are cultured in a medium containing an effective amount of a Factor VIII:c-stabilizing substance comprising (a) von Willebrand Factor (VWF), (b) a phospholipid or phospholipid mixture, or a mixture of (a) and (b).

6 Claims, 8 Drawing Sheets

OTHER PUBLICATIONS

Andersson et al, Biochemical Journal 200 pp. 161–167 (1981).

Lynch et al, Cell 41 pp. 49–56 (1985).

Wood et al, Nature 312 pp. 330–337 (1984).

Vehar et al, 1984, "Structure of human factor VIII," Nature 312:337–342.

Gitschier et al, 1984, "Characterization of the human factor VIII gene," Nature 312:326–330.

Toole et al, 1984, "Molecular cloning of a cDNA encoding human antihaemophilic factor," Nature 312:342–347.

Gitschier et al, 1984, "Detection and sequence of mutations in the factor VIII gene of haemophiliacs," Nature 315:427–430.

Lawn, Sep. 1985, "The Molecular Genetics of Hemophilia: Blood clotting factors VIII and IX," Cell 42:405–406.

Eaton, et al., 1986, "Proteolytic Processing of Human Factor VIII . . . ," Biochem 25:505–512.

Fass et al., 1985, "Internal duplication and sequence homology in factors V and VIII," Proc Natl Acad Sci USA 82:1688–1691.

Verweij et al., 1985, "Construction of cDNA coding for von Willebrand factor . . . ," Nucleic Acids Research 13(13):4699–4717 (partial cloning).

Bonthron, et al., 1986, "Nucleotide Sequence of pre--pro- von Willebrand factor cDNA," Nucleic Acids Research 14(17):7125–7127 (sequence).

Collins et al., 1987, "Molecular cloning of the human gene for von Willebrand factor . . . ," Proc Natl Acad Sci USA 84:4393–4397.

Levene, et al., 1987, "Expression of abnormal von Willebrand factor . . . ," Proc Natl Acad Sci USA 84:6550–6554.

Verweij, et al., 1987, "Expression of variant von Willebrand factor (vWF) cDNA . . . ," EMBO J. 6(10):2885–2890.

Hoyer, 1981, "The Factor VIII Complex: Structure and Function," Blood 58(1):1–13.

Hoyer & Trabold, 1981, "The effect of thrombin on human factor VIII," J. Lab. Clin. Med. 97(1):50–64.

Peak, 1984, "The nature of factor VIII," Clin Science 67:561–567.

Tuddenham et al, 1979, "The properties of factor VIII . . . ," J. Lab Clin Med 93:40–53.

Rick & Hoyer, 1977, "Thrombin Activation of factor VIII:I," Brit J Haematol 36:585.

Rick & Hoyer, 1978, "Thrombin Activation of factor VIII:II," Brit J Haematol 37:107.

Bloom, 1979, "The biosynthesis of factor VIII," Clin Haematol 8:53–77.

Kaufman et al, 1987, "Synthesis, Processing, and Secretion of Recombinant Human Factor VIII Expressed in Mammalian Cells," J Biol Chem 263(13):6352–6362.

Kaufman et al, "Expression and Chracterization of Factor VIII Produced in Mammalian Cells by Recombinant DNA Technology," in Proceedings of the Symposium on Biotechnology and the Promise of Pure FVIII (Roberts, ed., Baxter Healthcare Publications, Belgium, 1988).

Pavirani et al, 1987, "Choosing a Host Cell for Active Recombinant Factor VIII Production Using Vaccinia Virus," Bio/Technology 5:389–392.

Sadler & Davie, 1987, "Hemophilia A, Hemophilia B, and von Willebrand's Disease," in The Molecular Basis of Blood Diseases, pp. 575–630 (WB Saunders CO, Stamatoyannopoulos et al eds).

- ● Defined medium only – from another experiment where cultures grew to $3 \times 10^5$ cells/mL (after 72h)
- ○ D + 80 μg/mL
- ■ D + 80 μg/mL x 2
- △ D + 80 μg/mL x 3
- □ D + 80 μg/mL x 4

METHOD FOR PRODUCING FACTOR VIII:C AND ANALOGS

This application is a continuation of application U.S. Ser. No. 06/942,338 filed on Dec. 16, 1986 now abandoned and which is a continuation-in-part of U.S Ser. No. 816,031, filed Jan. 3, 1986 now abandoned, which is hereby incorporated by reference herein.

BACKGROUND OF THE INVENTION

The Factor VIII complex has two distinct biologic functions coagulant activity and a role in primary hemostatis. The analysis of Factor VIII deficiency diseases, classic hemophilia and von Willebrand's disease, have contributed to the understanding that Factor VIII is a complex of two components. The Factor VIII:c procoagulant protein (antihemophilic factor) and the Factor VIII related antigen (von Willebrand factor, VWF) are under separate genetic control, have distinct biochemical and immunologic properties, and have unique and essential physiologic functions.

The Factor VIII:c molecule is an important regulatory protein in the blood coagulation cascade. After activation by thrombin, it accelerates the rate of Factor X activation by Factor IXa, eventually leading to the formation of the fibrin clot. Deficiency of Factor VIII:c (classic hemophilia) is an X-linked chromosomal disorder that has been a major source of hemorrhagic morbidity and mortality in affected males. Treatment usually consists of frequent transfusions with blood products. The latter has resulted in a high incidence of infectious complications (such as various forms of hepatitis and acquired immunodeficiency disease) in the hemophiliac population.

The VWF molecule is an adhesive glycoprotein that plays a central role in platelet agglutination. It serves as a carrier for Factor VIII:c in plasma and facilitates platelet-vessel wall interactions. Discrete domains of VWF which bind to platelet receptor sites on glycoprotein 1b and on the glycoprotein IIb-IIIa complex, as well as binding sites on collagen have been noted. VWF is made up of multiple, probably identical, subunits each of 230,000 daltons. VWF is synthesized in endothelial cells and megakaryocytes. In the plasma it exists as high molecular weight multimers ranging from $5 \times 10^5$ to $10^7$ daltons. The Von Willebrand factor contains 5-6% complex carbohydrate, which appears important in the molecules ability to bind platelets. A variety of abnormalities in VWF activity can result in Von Willebrand's disease. The disorder is generally inherited in autosomal dominant fashion and may affect as many as one in 2000 individuals. Mild forms of the disease frequently go undiagnosed, whereas severely affected patients may require frequent blood product support with its associated risks.

Recently, the isolation of the genes for both factor VIII:c and Von Willebrand factor have made feasible the production of recombinant factor VIII:c and VWF preparations which are essentially free of contaminating viruses (Toole et al. 1984, Wood et al. 1984, Lynch et al. Cell 41:49-56 1985, Ginsberg et al. Science 228:1401-1406 1985). The production of Factor VIII:c through recombinant DNA technology has been achieved utilizing mammalian cells as a recipient of DNA encoding Factor VIII:c contained in appropriate expression sectors. One primary concern for the synthesis of a recombinant Factor VIII:c is its stability in the absence of the associated VWF protein Evidence to date indicates either that the VWF may have a stabilizing effect on the Factor VIII:c in plasma, or that the VWF can ellicit the release from storage depots or stimulate the synthesis and/or secretion of Factor VIII:c (Weiss, H. J. et al. 1977, J. Clin. Invest. 60: 390-404).

It has now been surprisingly discovered that suitably engineered mammalian cells produce significant levels of stable Factor VIII only in the presence of media containing a hydrophobic substance such as certain phospholipids or VWF, as is the case when the cell culture media contains serum. The Factor VIII:c synthesized in the absence of VWF or suitable phospholipids exhibits dramatic instability. VWF has been identified as one of the stabilizing components in serum. The gene for VWF has been expressed in a mammalian host cell to derive a protein which has the capability to stabilize Factor VIII:c expresssed in cells which are grown in the absence of serum. The expression of both Factor VIII:c (or analogs thereof) and VWF in mammalian cells allows for the production in improved yield of stable recombinant Factor VIII (or analogs thereof) in cells propagated in the substantial absence of serum.

SUMMARY OF THE INVENTION

This invention concerns an improved method for the production of recombinant Factor VIII:c. The method utilizes mammalian cells which contain DNA encoding Factor VIII:c and which are capable of expressing the Factor VIII:c. In accordance with the method of this invention the genetically engineered cells are cultured in media containing an effective amount of a Factor VIII:c stabilizing substance. Such substances include mammalian von Willebrand Factor (VWF); a stabilizing phospholipid or phospholipid mixture and mixtures of VWF and phospholipid(s). Preferred effective amounts of VWF range from about 0.1-10 ug VWF/ml media, with 1-3 ug/ml being specially preferred. One readily obtainable source of suitable phospholipids comprises commercially available dry milk preparations such as dried skim milk and low-fat skim milk. Such dried milk preparations may be added to the media in amounts ranging from about 0.01%-10% (weight of dry milk/volume of media). For optimal effect on Factor VIII production with minimal toxic effect on the cells, about 1%-3% dry milk is presently preferred. The dry milk preparations may be conveniently sterilized by first preparing a 10% aqueous solution/suspension of the milk and autoclaving.

"Phospholipid" as the term is used herein means an ester of phosphoric acid containing one or two molecules of fatty acid, an alcohol and a nitrogenous base. Examples of such phospholipids include Cephalin, phosphatidyl serine phosphatidyl choline mixtures, phosphatidyl inositol, soybean lecithin and mixtures thereof, with soybean lecithin being especially preferred. Other phospholipids useful in this method as well as effective and/or optimal concentrations and/or mixtures thereof may be readily identified by those skilled in the art using methods described in greater detail hereinafter. Presently preferred effective amounts of phospholipid or phospholipid mixtures comprise about 1-1000 ug phospholipid or phospholipid mixture per ml of culture media, with concentrations greater than about 100 ug/ml being more preferred and concentrations between about 200-300 ug/ml being especially preferred. Additionally, it is presently preferred to add the phospholipid or mixture to the culture media in the form of liposomes, preferably having a diameter of up to about 500 nm. Preferably the liposomes are unilamellar, although multilamellar liposomes may also be used. Most preferably the diameter of the liposomes is less than about 100 nm. Furthermore, liposomes made by conventional methods from said phospholipids may be used, either in admixture with or containing Factor VIII:c, as a carrier or vehicle for administering the protein to patients. Where dried milk is used as the source of phopholipids, the dried milk may be added directly to the media instead of the above-described liposomes.

VWF may be obtained from mammalian, e.g., human, bovine, porcine, etc., serum by conventional methods. Alternatively, "recombinant" VWF (i.e., VWF derived from genetically engineered cells) may be used. In one embodiment, suitably engineered VWF-producing cells are cultured in the medium to condition it with VWF either prior to or simultaneously with the culturing of the Factor VIII:c producing cells. Alternatively the recombinant VWF may be separately produced and added as an exogenous supplement to the media to be used for culturing the Factor VIII:c producing cells. In another embodiment the cells which produce Factor VIII:c are suitably engineered, i.e. effectively transformed with a VWF transcription unit, such that the VWF and the Factor VIII:c are co-expressed by the same cells. In a further embodiment of this invention the media used for culturing the Factor VIII:c producing cells contains both VWF, by virtue of one of the above-mentioned processes, and stabilizing phospholipid(s). In that case, it may be desirable to use reduced amounts of each component relative to the amounts used if used alone. By using appropriately supplemented defined media in accordance with this invention high levels of recoverable, stable Factor VIII:c activity are produced which may then be recovered and purified without the necessity for separation of serum components therefrom. However, the culture media used in this invention may additionally contain mammalian-derived serum, e.g. fetal bovine serum, in amounts up to about 10% (W/V), although amounts between 0 and 1% are somewhat preferred, and essentially serum-free media is especially preferred. Other conventional media supplements may also be added.

The method and attendant advantages (e.g. ease of purification, lower cost, greater stability, etc.) of this invention may also be used in the production of Factor VIII-like molecules Factor VIII-like molecules, as the term is used herein, mean proteins exhibiting procoagulant activity and which are encoded for by DNA sequences capable of hybridizing to DNA encoding Factor VIII:c. Such proteins, for example, may contain amino acid deletions between the 90 Kd and 69 Kd cleavage sites with respect to native Factor VIII:c, as described in greater detail in International Application No. PCT/US86/00774, published 23 Oct. 1986. Factor VIII-like molecules also include Factor VIII:c analogs containing amino acid deletions between the 50/40 cleavage site and the 69 Kd cleavage site which may be produced by methods analogous to those disclosed in PCT/US86/00774 Factor VIII-like molecules further include analogs wherein one or more of the arginine residues at positions 226, 336, 562, 740, 776, 1313, 1648 or 1721 have been replaced with different amino acids by conventional site-directed mutagenesis.

EXAMPLE I

Figure 1:
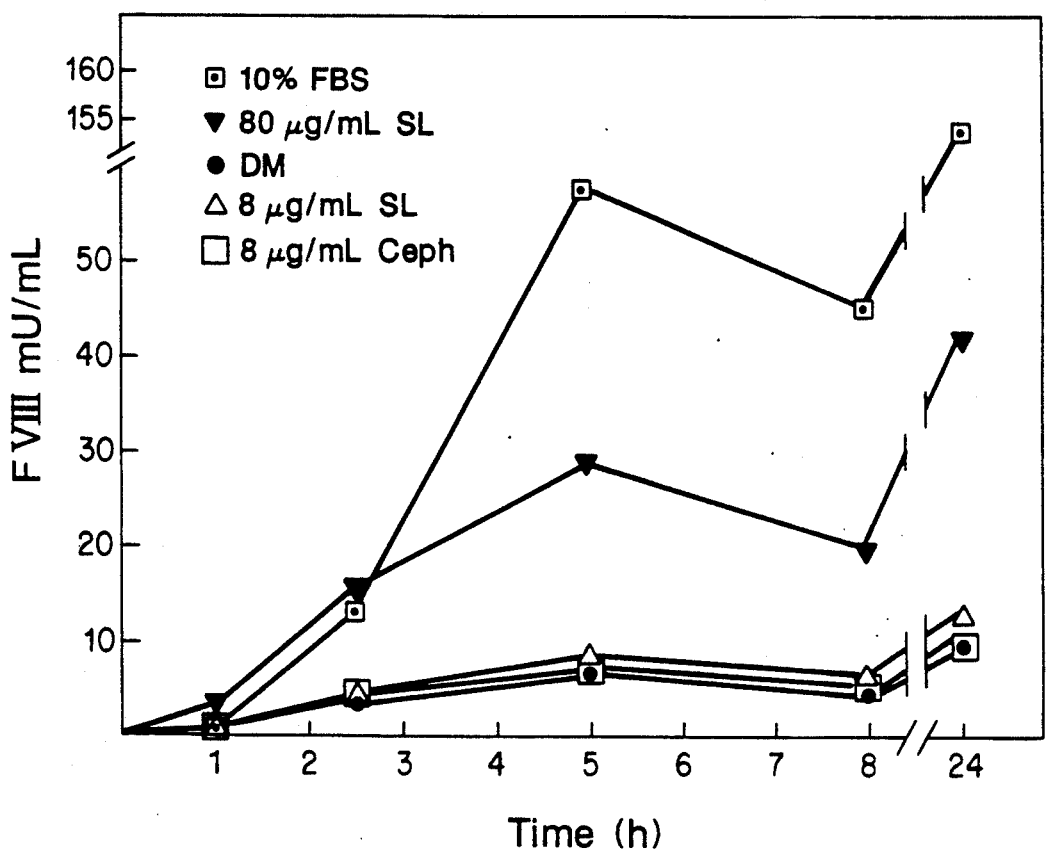
FIG. 1 illustrates the increase in rFactor VIII:c activity by phospholipid in the absence of fetal bovine serum. CHO cells (1E6 in 0.1 uM MTX) were suspended at a cell density of $3 \times 10^5$ cells/ml in defined medium and incubated in the presence of 10% fetal bovine serum, □; 80 ug/ml soybean lecithin, ▼; defined medium only, ●; 8 ug/ml soybean lecithin, Δ; 8 ug/ml of cephalin ▫. Phospholipids (PL) were solubilized by sonication of dried PL into 150 mM NaCl and added to growth medium from 10X concentrated stocks after filtration through a 0.22 um filter.

Establishment of Chinese Hamster Ovary Cell Lines which Express Human Factor VIII:c The Factor VIII:c expression plasmid used in this Example was RxPy VIII-I which contains in clockwise order the polyomavirus enhancer, the first leader sequence of the adenovirus tripartite leader sequence, a Factor VIII:c transcription unit followed by a DHFR gene and SV40 polyA tail, and a gene encoding tetracycline resistance. This plasmid was introduced into dihydrofolate reductase (DHFR) deficient Chinese hamster ovary cells by cotransformation with a DHFR expression plasmid and subsequent selection for cells that grow in the absence of added nucleotides. One particular pool of transformants designated lig 1 was subsequently grown in increasing concentrations of methotrexate (MTX) in order to amplify the DHFR and Factor VIII genes. The resultant cell line expressed high levels of Factor VIII activity as determined by either the ability to clot Factor VIII deficient plasma (Clotech assay) or by the ability to generate Factor Xa in the presence of Factor IXa, phospholipid, calcium, and Factor X (Cobas assay). The ability of these CHO cells to produce Factor VIII:c is shown in Table I. The Factor VIII activity increased 10,000 fold with increasing levels of MTX resistance which correlated with the Factor VIII gene copy number. Other expression vectors may also be used in place of RxPy VIII-I so long as they are capable of directing the expression of Factor VIII:c or analogs thereof. Such vectors include, for example, pCVSVL2-VIII (ATCC No. 39813, see European Application No. 85202121.1) and pDGR-2 (ATCC No. 53100, see PCT/US86/00774-deletion analog) Other Factor VIII:c expression vectors may be prepared using conventional expression vectors and techniques containing, for example, the SalI fragment from pCVSVL2-VIII or pSP64-VIII (ATCC No. 39812). The SalI fragment from either vector contains a DNA sequence encoding full-length Factor VIII:c.

TABLE I

Factor VIII Expression in Transfected and Amplified CHO cells.

| Pool | MTX (uM) | mU/ml/day of VIII:c |
|---|---|---|
| Lig 1 | 0.0 | 0.1 |
| | 0.02 | 11.5 |
| | 0.1 | 88.0 |
| | 1.0 | 288, 545* |
| | 5.0 | 644, 875* |
| | 20.0 | 1075 |

*Represents samples from two independent assays.

Plasmids pAdD26SVpA(3) (Kaufman and Sharp, 1982, Mol. Cell. Biol.) and plasmid pRXPy-VIII-I were digested with Cla 1 and the resultant linearized DNA was ligated in vitro and coprecipitated with CaPO4 and used to transfect CHO DHFR deficient DUKX-BII cells. Cells which efficiently expressed DHFR would be expected to contain the enhancer element from pRXPyVIII-I associated with the DHFR gene from pAdD26SVpA(3). Results have been consistent with this hypothesis. Subsequent selection for increased DHFR expression by propagation of the cells in increasing concentrations of MTX results in cells which have amplified the Factor VIII gene and the DHFR gene. At each level of MTX selection, samples of the conditioned media (approximately $10^6$ cells/ml in alpha media supplemented with 10% fetal bovine serum) were taken for Factor VIII:c activity assay determined by the Kabi Coatest method modified to obtain sensitivity better than 0.05 mU/ml. Comparable results were also obtained by the one-stage activated partial thromboplastin time (APTT) coagulation assay using Factor VIII:c deficient plasma. All samples exhibited thrombin activation of 30–50 fold. For thrombin activation, the samples were pretreated 1–10 min with 0.2 units/ml thrombin at room temperature.

EXAMPLE II

Serum Dependence of Factor VIII:c Synthesis

CHO cells (Lig 1 2αA subclone B10 in 0.1 uM MTX at 80% confluence) which are rinsed and fed with media containing 10% FCS or defined media (serum free, containing: 5 mg/ml BSA, insulin, transferrin, selenium, hydrocortisone and putrescine) accumulate Factor VIII activity. The rate of appearance in defined media is roughly 4-fold lower than in serum-containing media. The 4-fold difference becomes larger as the cells are propagated in the absence of serum. This results from inefficient rinsing of the cells. The rate of Factor VIII:c appearance increases fairly linearly up to 24 hrs. which suggests the VIII is stable in the media. This result is similar to results obtained with COS cells at lower levels of VIII expression (Approx. 10 mU/ml/day)

Cephalin, a mixture of phospholipids, can counteract at least part of the serum deficiency. CHO cells (Lig. 2αA pool in 20 uM MTX) were fed + or −5 uM cephalin for an additional 2 hr. Media was assayed at 6 hrs. and 25 hrs. and results shown below:

```
0 time
   |___+ or − serum___|___+ ceph_____19 hr.
Rinse    4 hr.        |    2 hr.
                      |___− ceph_____19 hr.
                           2 hr. /|\       /|\
                               Assay (6 hr.)  Assay (25 hr.)
```

| Conditions | | | |
|---|---|---|---|
| Serum | Cephalin | 6 hr. | 25 hr. |
| +FCS | +Ceph | 594 | 1044 |
| −FCS | +Ceph | 408 | 514 |
| +FCS | −Ceph | 563 | 1492 |
| −FCS | −Ceph | 140 | 372 |

The results suggest that cephalin alone can increase VIII activity in the absence of serum but that its effect is short lived (i.e. observed after 2 hrs. but is diminished at 25 hrs.). In one experiment the concentration of cephalin was increased and there was no further increase in VIII activity. This indicated some component in the cephalin was not rate limiting.

Part of the cephalin effect can be elicited by a simpler mixture of phospholipids or by single phospholipids. Cells (Lig 1 2αA 0.02 pool in 20 uM MTX) were fed with 10% fetal calf serum or serum free media for 24 hrs. and then either cephalin (5um) or a mixture (1:4) of phosphatidyl serine and phosphatidyl choline (PCPS) were added to serum free cultures. Results from media assayed after 2 hrs. were:

| Serum Free | 110 |
|---|---|
| Serum Free + Cephalin | 489 |
| Serum Free + PCPS | 230 |
| 10% FCS | 613 |

This result demonstrates that phospholipids alone can increase VIII activity in conditioned media.

Analysis of the thrombin activability of VIII expressed in CHO cells growing under different conditions suggests that the presence of serum decreases the degree of thrombin activation. CHO cells (Lig 1 2αA pool in 20 uM MTX) were rinsed and fed with media containing 10% fetal calf serum or defined media (5mg/ml BSA, transferrin, selenium, insulin, hydrocortisone, putrescine). 24 hrs. later either cephalin or 10% FCS was added and 2 hrs. later samples taken for assay and measure of thrombin activatibility:

| | | Assay at 26 hrs. | | |
|---|---|---|---|---|
| Sample Media | Added at 24 h | Cobas mU/ml | mU/ml | Coagulation Assay (fold activation) |
| Defined media | — | 315 | 300 | 20X |
| Defined media | 5 uM cephalin | 752 | 1040 | 34X |
| Defined media | 10% FCS | 684 | 440 | 8.4X |
| +10% FCS | — | 1078 | 1200 | 10X |
| +10% FCS | 5 uM cephalin | 1154 | 1120 | 14X |
| Defined media | 10% boiled FCS | 543 | — | — |

These results indicate that the presence of serum increases the activity produced compared to serum free media but reduces the thrombin activatibility. In contrast, cephalin can compensate for the serum effect on increasing the activity of the VIII produced but does not reduce the thrombin activatibility. Thus, in serum free media, with the addition of cephalin 2 hrs. prior to harvest, CHO cells produce VIII at 1 unit/ml and this material exhibits a 34 fold thrombin activation. This experiment also demonstrates that 10% FCS added to serum free media 2 hrs. prior to assay can also increase the amounts of VIII activity. This ability was not diminished by boiling the serum 10 min prior to its addition Thus, the serum factor required for VIII activity is heat stable We conclude that the serum factor required for increasing VIII may comprise two components: a phospholipid and another, heat stable factor which may be required to stabilize the phospholipid.

In order to determine if serum affects secretion, synthesis, or some other process in VIII production, cells were labeled with $^{35}S$ methionine in serum containing or serum free media and intracellular and secreted protein was analyzed after immune precipitation and gel electrophoresis. Results from analysis of the intracellular protein have shown no effect on VIII synthesis or processing by monitoring the presence of the 230K and 76K doublet when labeled in the presence or absence of serum or in the presence or absence of cephalin Experiments were conducted comparing VIII protein synthesized and secreted in serum free or serum containing media after immunoprecipitation with the hybri-tech monoclonal (anti 76K) which reacts with the light chain or the 200K monoclonal (F81.2.1) which reacts with the heavy chain and gel electrophoresis. Surprisingly, although VIII activity in these experiments is 4-fold greater in serum-containing media than in serum free media, there is little difference in the amount of the 76K doublet precipitated by the 76K antibody (hybri-tech) or the 200K smear precipitated by the 90K antibody (F8 1.2.1) upon analysis of the labeled culture media. The only observable differences between the serum-free and serum containing samples are 1) the presence of a minor 76 doublet in serum containing media upon precipitation with the anti 200K antibody (F8.1.2.1), 2) the presence of a minor 200K smear in serum containing media upon precipitation with the anti 76K antibody (hybritech), and 3) the presence of a single band migrating with the lower band from the 76K doublet in serum-free media upon precipitation with the 200K monoclonal (F8.1.2.1). The majority of these results conform to a hypothesis summarized below.

The results are explained if the active VIII represents an association of the 200K fragment with the 76K fragment both of which appear in the media due to intracellular cleavage of the precursor The association is stabilized by a factor in serum, possibly phospholipid, but can be disassociated upon reduction and polyacrylamide gel electrophoresis but not upon immunoprecipitation. The results also suggest, from the band intensities of the 190K and 76K doublet, that only a fraction (possible 20%) of the VIII produced in CHO cells is active (measured by percent of the 76K and 190K polypeptides which are associated together) even in the presence of serum. This hypothesis is consistent with results from other antibodies upon precipitation of labeled VIII from conditioned media containing serum.

To determine whether the 10% serum was limiting for Factor VIII:c expression in the highly amplified CHO cell lines, we monitored the effect of increasing amounts of serum on the ability to elicit factor VIII:c activity in the cell line 10A1. 10A1 is a clone derived from selection of the Lig 1 pool for growth in 1 mM MTX. This experiment demonstrated the effect on Factor VIII activity of adding increasing amounts of fetal bovine serum to the 10A1 cells for 24 hrs. 50% serum yielded three-fold more activity in the 24 hr. conditioned media compared to 10% serum. Other results have indicated that the amount of active Factor VIII antigen is correspondingly increased when cells are propagated in 50% serum. Other cell lines, which express slightly lower levels of Factor VIII:c show less dramatic increases in Factor VIII c activity upon growth in higher concentrations of serum. Thus there appears to be some limiting requirement for Factor VIII: expression in these higher producer cells.

EXAMPLE III

Serum Dependence of rFactor VIII:c Synthesis in Suspension Cultures of CHO

The following table illustrates the dependency of recombinant Factor VIII:c (rFVIII) activity on serum levels in culture. A relatively low rFVIII producer, clone 1EG, was grown in suspension culture for 3 to 4 days in medium containing various concentrations of fetal bovine serum (FBS).

| Serum Concentration in Medium* | rVIII Activity (mU/ml) after 3-4 days | Average Productivity (U/$10^6$ cells/day) |
|---|---|---|
| 10% FBS | 318 | 0.19 |
| 5% FBS | 100 | 0.03 |
| Defined* | 4 | 1/4-0.01 |

*RPMI 1640 was employed as basal medium for all of the above. The defined medium consists of insulin, 5 ug/l; transferrin, 5 ug/ml; serenium, 5 ng/ml; hydrocortisone, $10^{-8}$ M, putrescene, 100 ng/ml; BSA, 5 mg/ml.

The same serum dependence has been observed with other CHO cell lines. These results do not reflect genetic instability since original expression levels can be regained on addition of serum.

Figure 2:
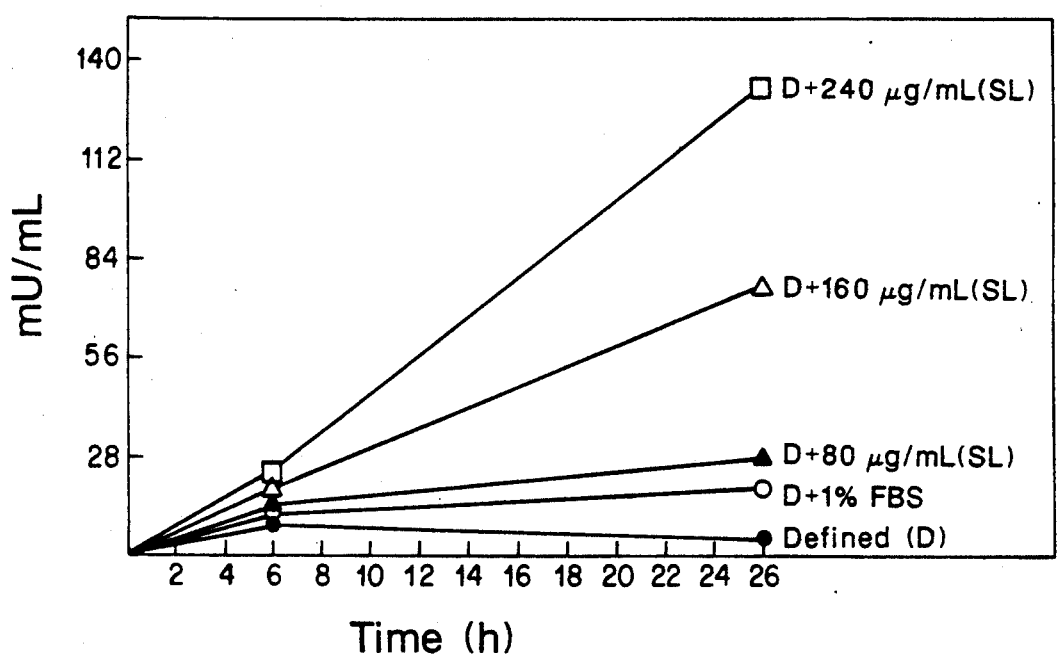
FIG. 2 illustrates the dependence of rFactor VIII:c activity on phospholipid concentration CHO cells (1E6) were suspended in defined or semi-defined medium (i.e. defined medium plus 1% FBS) in the presence of various concentrations of soybean lecithin. ●-defined medium only; 0-defined medium plus 1% FBS; ▲-defined medium plus 1% FBS plus 80 ug/ml soybean lecithin; Δ-defined medium plus 1% FBS plus 160 ug/ml of soybean lecithin; □-defined medium plus 1% FBS plus 240 ug/ml of soybean lecithin.

As can be seen from FIG. 1, addition of phospholipid to culture medium can replace the serum requirement, however relatively high concentrations of phospholipid are required (on the order of 10-20 fold higher than previously used with serum-containing media). The concentration dependence of FVIII activity on phospholipid is illustrated in FIG. 2. Signifcantly the level of rFVIII generated over a 26h period in the presence of 240 ug/ml of soybean lecithin (SL) is similar to that generated in a similar experiment described in FIG. 3 in the presence of 10% FBS. Increasing the concentration of SL above 240ug/ml resulted in no further increase in rVIII activity.

Such high concentrations of SL may have been required because a specific component of this phospholipid mixture, present in relatively small quantities, was effective in increasing r FVIII:c activity Accordingly, a number of better defined phospholipids were added to cultures in completely defined medium, either singly, or in combination, to establish if any would effect a more pronounced increase in rFVIII activity However, as can be seen from the following table, soybean lecithin is the most effective phospholipid of those considered (including cephalin).

In order to optimize a PL addback scheme which would allow for the production of maximum levels of FVIII while minimizing the potential toxic side effects of the added phospholipid the following experiment was designed.

Experimental Design for Soybean Lecithin add-back to defined and semin-defined medium

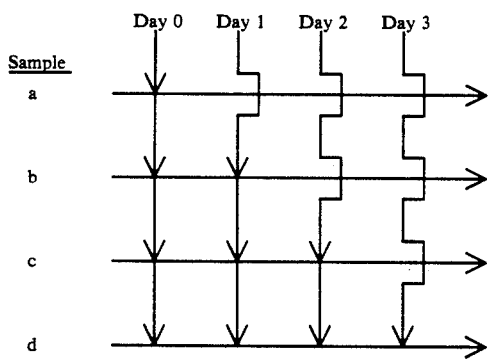

Figure 3:
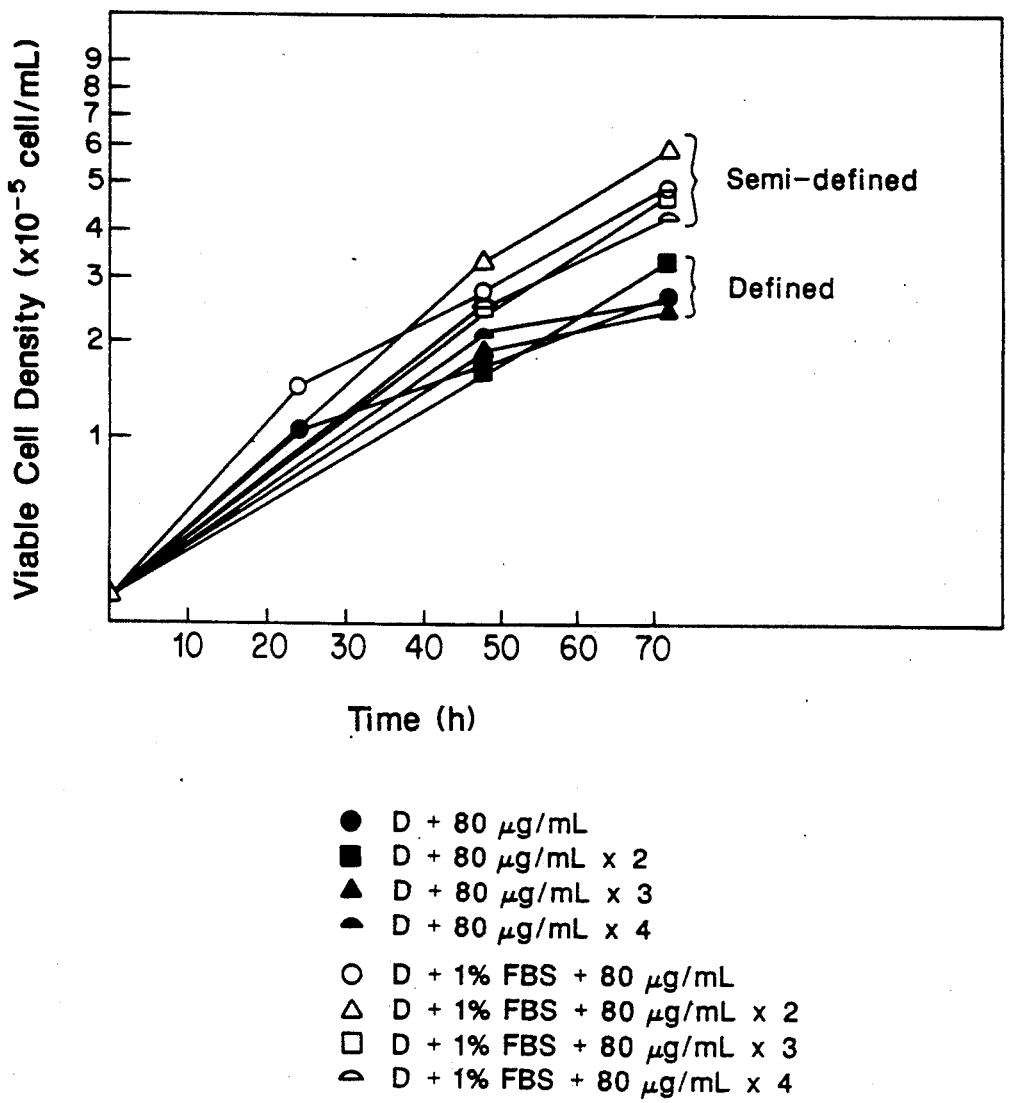
FIGS. 3 & 4 illustrate the growth of 1E6 cells in phospholipid-supplemented defined and semi-defined media, and the production of rFactor VIII from 1E6 in phsopholipid-supplemented defined media respectively. Cultures were grown in 25 ml spinner flasks and phospholipids were added where indicated.
Figure 4:
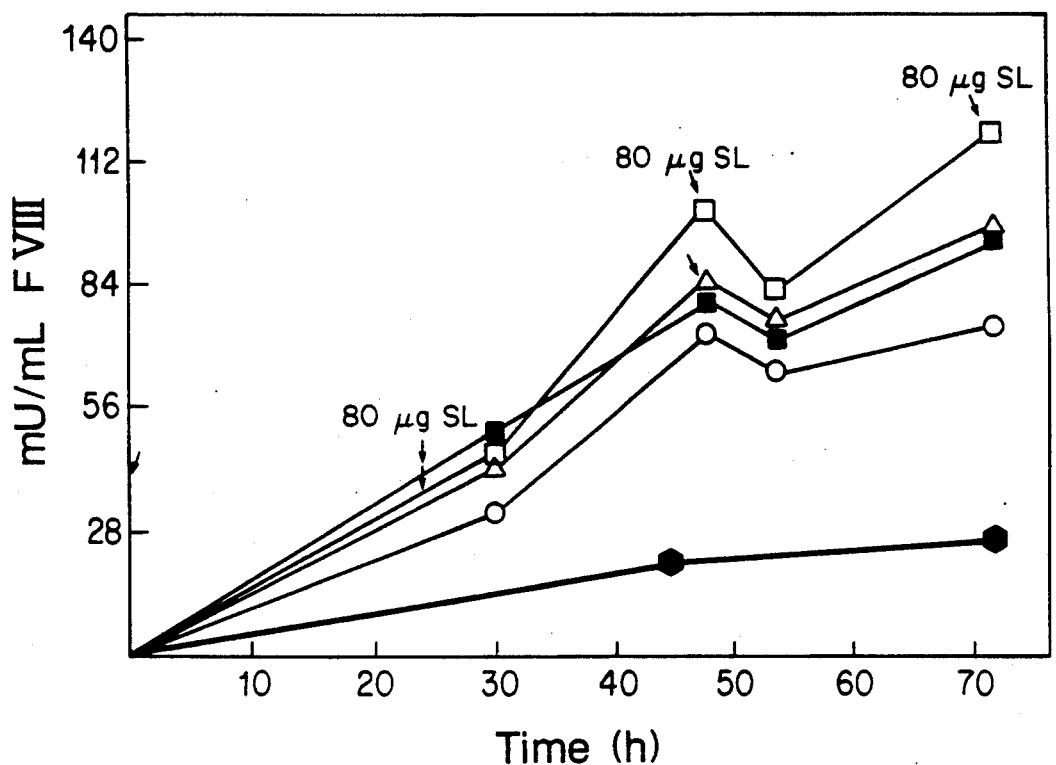

On day 0 890 ug/ml of Pl was added to all the cultures, on day 1 PL was added to all the cultures apart from a, and so on. FIGS. 3 and 4 show growth and rFVIII production data resulting from this experiment. FIG. 3 shows the growth curves of CHO cells (1EG) in semi-defined and defined media in the presence of various concentrations of phospholipid

| Phospholipid supplement (ug/ml added) | Cell density ($\times 10^5$ cells/ml culture) | Viabilities | FVIII (mU/ml) After 24 h in culture |
|---|---|---|---|
| Cephalin (240) | 7.9 | 98 | 42 |
| Cephalin (240) | 7.8 | 97 | 45 |
| PS:PC:PI (240) (59%:25%:25%) | 8.8 | 95 | 34 |
| PS:PC:PI (1/2-120) | 9.1 | 96 | 35 |
| PC:PS (240) | 9.0 | 94 | 38 |
| PC:PS (120) | 7.5 | 98 | 45 |
| PS:PI (240) (50%:50%) | 9.5 | 95 | 6 |
| PS:PI (120) | 9.2 | 96 | 17 |
| PC:PI (240) (50%:50%) | 8.4 | 92 | 54 |
| PC:PI (120) | 7.6 | 94 | 69 |
| Soybean Lecithin (240) | 8.6 | 94 | 130 |
| Soybean Lecithin (120) | 9.5 | 95 | 106 |

Phospholipids were added back to cultures of CHO (1EG) in completely defined medium at a cell density of $5 \times 10^5$ cells/ml from 100x stock solutions in 150 mM NaCl. Phospholipids (PL) were solubilized by sonication of dried PL into 150 mM NaCl followed by passage (x3) through a french press. The resulting liposome solution was filtered through a 0.22 um filter prior to use. PS=phosphatidyl serine; PC=phosphatidyl choline; PI=phosphatidyl inositol.

The addition of phospholipid causes no marked changed in cell growth in either medium (FIG. 3). FIG. 4 shows that maximum rFVIII activity is obtained in the culture where 320 ug/mL was added back (4×80 ug/mL). In semi-defined medium maximum, levels of 195 mU/mL were obtained after 72 h where 240 ug/mL (3×80 ug/mL) of soybean lecithin was added. These and other data illustrate that soybean lecithin added stepwise to cultures on days 0, 1, 2 and 3 allowed production of rFVIII. The optimum concentrations were between 240–320 ug/mL in these experiments where phospholipid was solubilized by sonication. When phospholipids were prepared by homogenization (manton-gaulin or french press) the optimum level was lower; 120–160 ug/mL.

The cellular productivities in two different CHO cell lines from experiments similar to the above are shown below.

| Medium | Average Productivity (u/$10^6$ cells/day) | (Cell Line-1EG) |
|---|---|---|
| 10% FBS | 0.19 | |
| 5% FBS | 0.03 | |
| Defined | 1/4-0.01 | |
| Defined + SL | 0.24 | |
| Defined + 1% FBS + SL | 0.25 | |

| Medium | Average Productivity* | (Cell Line-H9.05) |
|---|---|---|
| 10% FBS | 0.43 | |
| Defined + 1% FBS + SL | 0.51 | |

*Units as above

Figure 5:
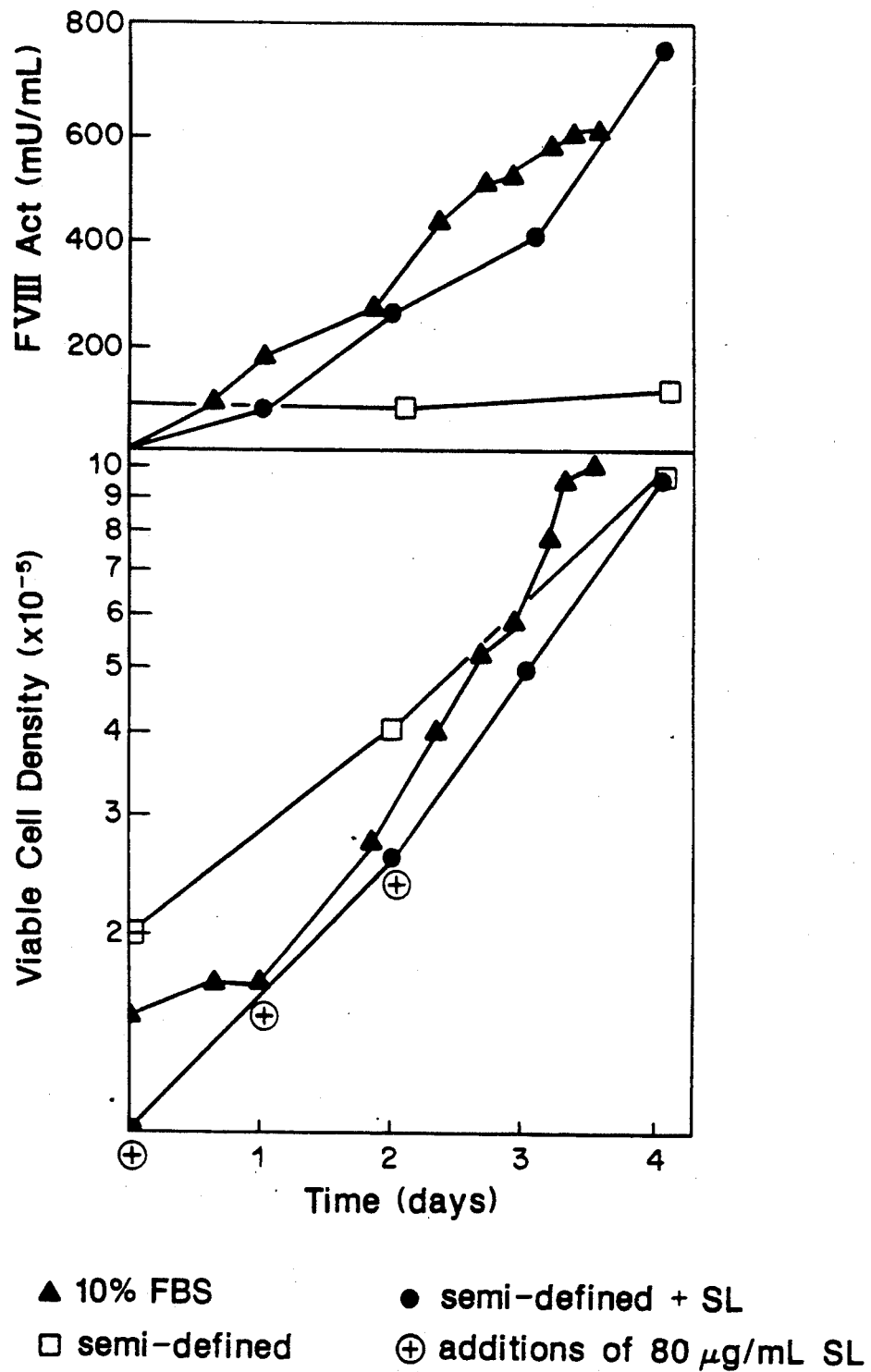
FIG. 5 illustrates the production of rFactor VIII from CHO cells in suspension culture, comparing growth and production in 10% serum supplemented and phospholipid-supplemented semi-defined media. The CHO cell line (H9.05) was grown in suspension culture either in 10% FBS supplemented medium (▲) or semi-defined medium in the absence (■) and presence (●) of soybean lecithin. 80 ug/mL equivalents of soybean lecithin were added where indicated.

Thus, productivities of rFVIII from rCHO cells are at least equivalent in defined medium supplemented with phospholipid as in serum containing medium However, as illustrated by the data above, the bulk quantity of rFVIII produced in defined medium is less than in serum containing medium. This is due to the fact that cells grow more rapidly and to higher cell densities in serum-containing medium rather than being more productive. On supplementation of defined medium with small quantities of serum (e.g. 1%) cell growth is improved. Indeed, after a short period of adaption cells will grow almost as well in semi-defined medium as in 10% FBS supplemented medium. FIG. 5 illustrates that a rCHO cell line (H9.05) grows to similar cell densities and is at least equally productive (in Factor VIII) in phospholipid supplemented semi-defined medium as in 10% FBS supplemented medium.

Role of Phospholipid

Figure 6:
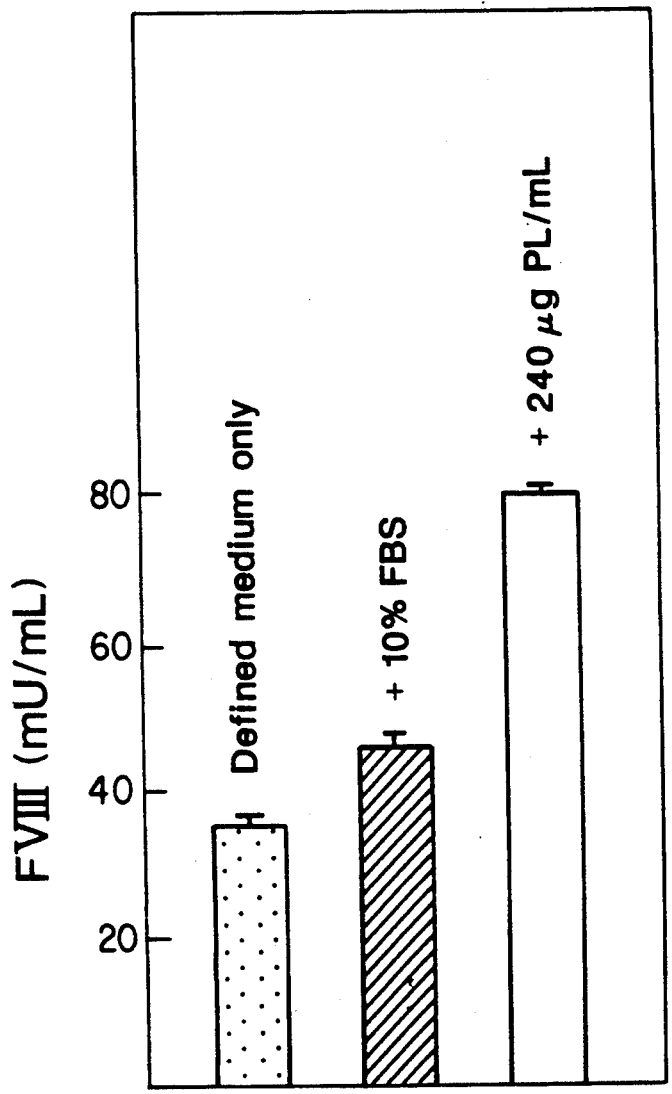
FIG. 6 illustrates the increase in rFactor VIII activity in defined medium resulting from supplementation with soybean lecithin.

Phospholipid may function by stabilizing rFVIII in defined medium in the absence of serum. CHO cells (1E6) were grown for 3 days in defined medium in the absence of phospholipid. When soybean lecithin was added to this medium (cell-fee) an increase in activity was seen after a 5 hour incubation (FIG. 6). In another experiment a comparable reactivation was observed within 30 min of phospholipid addition.

Figure 7:
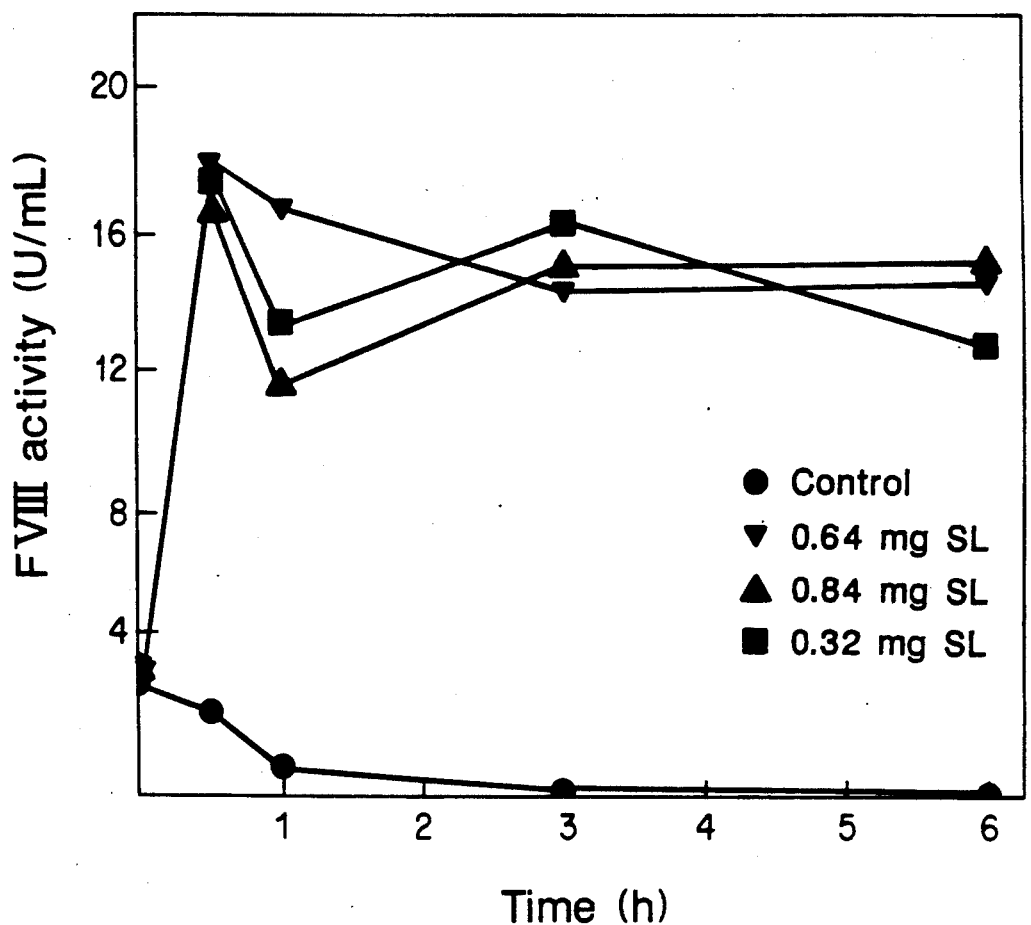
FIG. 7 illustrates the activation and stabilization of Factor VIII by phospholipid To 50 ul of rFIII in 50% ethylene gycol and 1M NaCl was added 0.64 mg (▼); 0.48 mg (▲) and 0.32 mg (■) of soybean lecithin from an 8 mg/mL stock in 150 mM NaCl. Samples were incubated at 37 degrees C. alone with a control which did not contain phospholipid (●).
Figure 8:
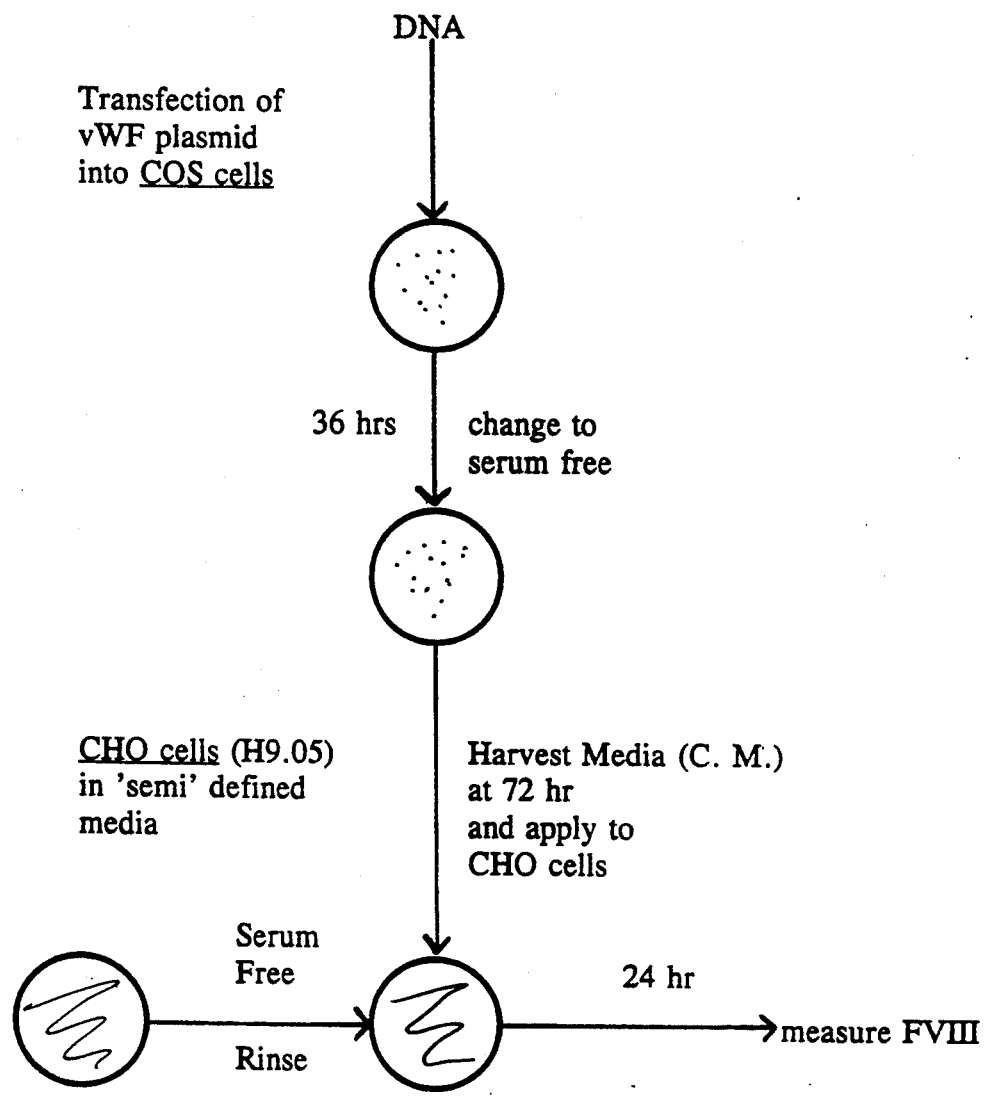
FIG. 8 illustrates the ability of recombinant VWF to elicit Factor VIII expression.

A further example of phospholipid reactive/stabilization was employed with partially purified rFVIII. Two samples of partially purified FVIII were examined-both in the presence of 50% ethylene glycol and 1M NaCl (used as an eluent in an affinity-purification step). Both samples were analyzed at about 20 U/mL FVIII activity directly after elution from the affinity column. One of the samples (A) was subjected to repeated freeze-thaw treatments resulting in loss of activity (activity reduced from approximately 10 U/mL to approximately 3 U/mL). Soybean lecithin was added to this inactivated rFVIII preparation resulting in a marked increase in activity and subsequent stabilization relative to a control which contained no added phospholipid (FIG. 7).

The other sample (B) which had not been allowed to inactivate (20U/mL at the start of the experiment) did not increase in activity on addition of phospholipid (added in same proportions as described in the legend to FIG. 7) but retained 100% activity for 24 h at 37 degrees C. A control which lacked phospholipid lost 99% of its activity (40 mU/mL) within 30 min.

These data indicate that phospholipid may stabilize rFVIII in a biologically active conformation and if denaturation of rFVIII has occurred phospholipid allows rFVIII to regain its biologically active conformation.

EXAMPLE IV

Porcine VWF can act to elicit Factor VIII:c activity from CHO cell propagated in the absence of serum Lig 1 (20 uM MTX) cells were rinsed and fed defined media (alpha media containing insulin, transferrin, serenium, hydrocortisone, and putrescine, glutamine, and penicillin and streptomycin) added back with increasing concentrations of bovine serum albumin or with similar concentrations of ovalbumin Table II. Both proteins can act to elicit Factor VIII:c expression. However, when partially purified VWF is added back to media containing 5 gl bovine serum albumin, the Factor VIII:c activity increased four-fold to even greater than the levels obtained upon propagation of the cells in 10% fetal bovine serum. This dramatically demonstrates the ability of VWF to elicit Factor VIII:c activity in the absence of serum. This result has been duplicated with different preparations of porcine VWF and also with purified human VWF.

In order to demonstrate that the ability to elicit factor VIII:c was due to VWF, the following experiment was performed. Cells which express Factor VIII:c were incubated in the presence of media containing serum derived from human VWF deficient plasma. Factor VIII:c activity in the CHO Lig 1 cells incubated in VWF deficient serum was 25% the level compared to normal human serum. When the porcine VWF preparation was added back to the VWF deficient serum, the Factor VIII activity increased to the 10% fetal bovine serum value. The effect could be elicited with as little as 2.50 ug/ml of VWF. See Table IIA. In another experiment, when the VWF concentration was decreased to 0.25 ug/ml, the activity was only 50% that of the 10% fetal bovine serum level.

TABLE II

FACTOR VIIIc EXPRESSION IN DEFINED MEDIA WITH VWF ADDED BACK TO Lig 1 CELLS

|  |  | Units/ml/day |
|---|---|---|
| Defined Media + | 0 | 0.164 |
| Ovalbumin (g/l) | 0.5 | 0.189 |
|  | 1.0 | 0.215 |
|  | 2.0 | 0.280 |
|  | 5.0 | 0.290 |
|  | 20.0 | 0.380 |
|  | 5.0 |  |
| with Porcine VWF at | 2.5 ug/ml | 1.200 |

TABLE II-continued

FACTOR VIIIc EXPRESSION IN DEFINED MEDIA WITH VWF ADDED BACK TO Lig 1 CELLS

|  |  | Units/ml/day |
|---|---|---|
| Defined Media + | 0 | 0.190 |
| Bovine Serum Albumin | 0.5 | 0.320 |
| (g/l) | 1.0 | 0.380 |
|  | 2.0 | 0.375 |
|  | 5.0 | 0.430 |
|  | 20.0 | 0.490 |
|  | 5.0 |  |
| with porcine VWF at | 2.5 ug/ml | 1.350 |
| 10% Fetal Bovine Serum |  | 0.978, 1.075 |

TABLE IIA

Effect of VWF on Factor VIII Production

| MEDIA | mU/ml/day |
|---|---|
| 10% fetal bovine serum | 1321 |
| defined media with 5 g/l bovine serum albumin | 342 |
| 10% normal human serum | 937 |
| 10% VWF deficient human serum | 246 |
| 10% VWF deficient human serum with porcine VWF added back at: |  |
| 2.5 ug/ml | 1124 |
| 20 ug/ml | 1397 |

In order to examine the effect of added VWF on the amount of Factor VIII:c in the conditioned media, cells were labeled with a 1 hr. pulse of 35-S methionine and chased in either media containing 10% fetal bovine serum, 10% VWF deficient human serum, or 10% VWF deficient human serum with porcine VWF added back. Results demonstrated that upon addition of VWF to VWF deficient serum, more Factor VIII:c (both the heavy 200 kDa and the light 76 kDa chains) was present in the media No change in the intracellular synthesis of Factor VIII:c was observed VWF addition to 10% fetal bovine serum resulted in no change in the level of Factor VIII:c in the conditioned media. These experiments indicate the VWF is necessary for the secretion and/or stability of Factor VIII:c.

EXAMPLE V

Expression of Human VWF in COS Cells

The cloning of a partial segment of the human VWF cDNA has previously been reported (Ginsberg, et al. 1985, Science). Subsequent to that report, the full length VWF cDNA has been assembled and its sequence determined. The cloning, sequence and expression of VWF have been described in detail in International Application No. PCT/US86/00760, published on 23 Oct. 1986. We have inserted the full length cDNA clone into the expression vector pMT2 to produce pMT2-VWF (ATCC No. 67122). pMT2-VWF contains the adenovirus associated (VA) genes, SV40 origin of replication including the transcriptional enhancer, the adenovirus major late promoter including the adenovirus tripartite leader and a 5' splice site, a 3' splice site derived from an immunoglobulin gene, the VWF coding region, a non-coding DHFR insert, the SV40 early polyadenylation site, and the pBR322 sequences needed for propogation in E. coli. Details of this vector, which is a derivative of pQ2, are provided in Kaufman, Proc. Natl. Acad. Sci., USA 82:689-693 (1985). pMT2-VWF DNA was then prepared for COS cell transfection by conventional methods. Sixty hours after DEAE dextran mediated transfection of COS cells, the cells were labelled with 35-S methionine and media and cell extracts were immunoprecipitated with a rabbit anti-human polyclonal antibody (Calbiochem) and precipitates analyzed by SDS reducing gel electrophoresis. Results demonstrate a significant amount of VWF is synthesized in the transfected COS cells, the majority of its being secreted In the conditioned media there is an approximately 260 kDa protein and a 220 kDa protein which resembles the completely processed form of VWF. Approximately 50% of the VWF synthesized is processed to the 200 kDa form. When analyzed for multimer formation by non-reducing gel electrophoresis, it was found the VWF was associated into multimers, but not of extremely high molecular weight like those seen in plasma. The multimers ranged up to 1 million daltons by a rough estimate Analysis of the VWF antigen in the COS cell conditioned media indicated the presence of human VWF at 0.35 ug/ml. Other analyses have indicated that the VWF expressed in COS cells specifically binds both platelets and collagen.

EXAMPLE VI

Recombinant VWF can elicit the expression of human Factor VIII:c

The VWF expression plasmid pMT2-VWF was transfected onto COS cells by DEAE dextran mediated transfection and 36 hours post-transfection, the media changed to serum free (DMEM lacking serum) (See FIG. 7). 72 hours later the COS cell conditioned media was harvested and applied to the CHO Lig 1 cells (20 uM MTX resistant) which were previously rinsed with serum-free media (at $10^6$ cells/ml). Twenty-four hours later the media was taken from the CHO cells and assayed for Factor VIII activity. The results are shown below and compared to Factor VIII:c activities from CHO cells propagated in 10% fetal bovine serum and in serum-free media for 24 hours.

| Media on CHO Lig 1 (20 uM MTX) | mU/ml Factor VIII:c |
|---|---|
| Conditioned media from mock transfected COS cells | 141 |
| Conditioned media from VWF transfected COS cells* | 423 |
| 10% Fetal Bovine Serum | 950 |
| Serum-free media | 30 |

*The conditioned media in this experiment contained 0.3 ug/ml of human VWF.

EXAMPLE VII

Introduction, Expression, and Amplification of VWF Genes in Chinese Hamster Ovary Cells which express Factor VII:c For expression of VWF in Chinese hamster ovary (CHO) cells, a second expression vector, pMT2ADA-VWF (ATCC #67172), was used with a protocol of selection for cells over-expressing the enzyme adenosine deaminase to amplify the plasmid sequences (Kaufman et al., 1986, Proc. Natl. Acad. Sci. 83:3136; U.S. Ser. No. 619,801). A factor VIII:c expressing cell line which was cloned from Lig 2αA (from example 1) in 1 mM MTX and designated 10AI, was used as recipient for transfer of pMT2ADA-VWF. pMT2ADA-VWF was introduced into 10Al cells by protoplast fusion as described (Sandri-Goldin et al., 1981, Mol. Cell. Biol. 1:743). E. coli DH5 cells harboring pMT2ADA-VWF (DH5 was used to minimize homologous recombination and deletion of the VWF sequences) were grown in 50 ml of L-broth containing 50 ug/ml ampicillin to an $A_{600}$ of 0.6. Chloramphenicol was added to 250 ug/ml and the culture incubated at 37° C. for an additional 16 hrs, in order to amplify the plasmid copy number. A suspension of protoplasts was prepared as described (Sandri-Goldin et al., 1981), added to 10Al cells at a ratio of approximately $1-2 \times 10^4$ protoplasts/cell, and centrifuged onto the cells at 2000 rpm for 8 minutes in an IEC model K centrifuge. After centrifugation, the supernatant was removed by aspiration and 2 ml of polyethylene glycol solution (50g of PEG 1450, Baker Chem. Co., in 50 ml of Dulbecco's modified medium) was added to each plate. Cells were centrifuged again at 2000 rpm for 90 seconds; the polyethylene glycol solution removed, and the plates rinsed 3 times in alpha medium containing 10% (v/v) fetal calf serum. Cells were then plated into tissue culture dishes in medium containing 100 ug/ml kanamycin, 10 ug/ml each of penicillin and streptomycin, and 20 uM MTX. Two days later the cells were trpysinized and subcultured 1:15 into ADA selective media with 10% dialyzed fetal calf serum, 0.1 um deoxycoformycin, 10 ug/ml of penicillin and streptomycin, and in the presence and absence of 20 uM MTX. The ADA selective media (AAU) contained 1.1 mM adenosine, 10 ug/ml alanosine and 1 mM uridine. Subsequently it was shown that removal of the MTX selection at this stage resulted in a decrease in the factor VIII:c expression. Subsequently, the MTX has been left in the ADA selective media.

It was possible to amplify the VWF gene by selection for growth in increasing concentrations of 2'-deoxycoformycin (dCF) in the presence of cytotoxic concentrations of adenosine. A pool of transformants (6 colonies) was selected for ADA in the presence of 20 uM MTX. The ADA selection media was changed by sequentially increasing the concentration of 2'deoxycoformycin (steps of 0.1 uM, 0.5 uM, 1.0 uM and 2.0 uM) in the presence of 20 uM MTX. At each step, the production of VWF and of factor VIII:c was measured after 24 hours in the presence of 10% fetal calf serum (FCS) or in defined media. The results are summarized below:

| Expression of VWF and Factor VIII:c in Coexpressing CHO cell lines. | | | | |
|---|---|---|---|---|
| | Selection | | VWF Antigen | Factor VIII:c |
| Cell line | dCF uM | MTX uM | ug/ml    pg/cell | uUnits/cell |
| 10A1 (no VWF) | | | | .38*<br>0.93** |
| 10A13A | 0.1 | 20 | 0.07    0.1 | |
| | 0.5 | 20 | 0.8    1.14 | 0.63*<br>0.89** |
| | 1.0 | 20 | 24    30 | 0.63*<br>1.1** |
| | 2.0 | 1000 | 7.4    24 | 1.4*<br>1.5** |

*in defined media;
**in media containing 10% Fetal calf serum
Legend: VWF antigen was determined by an ELISA assay using affinity-purified rabbit-anti-VWF antiserum (Calbiochem-Behring, 782301), purified VWF antigen from normal human plasma pools to serve as standards and controls, and IgG isolated from Calbiochem-Behring, 782301, and conjugated with alkaline phosphatase. Factor VIII:c activity was determined by the chromogenic assay described in Example 1.

These results demonstrate that VWF expression increased with increasing ADA selection. In addition, expression of factor VIII:c was not dependent on the presence of serum, as observed by line 10A13aA in 2 uM dCF and 1000 uM MTX which expresses 1.4 uUnits/cell/day of factor VIII:c in defined media.

EXAMPLE VIII

Fusion of CHO cells expressing Factor VIII:c and CHO cells expressing VWF

The VWF gene has been introduced into CHO DHFR deficient cells (DUKX-B11, Chasin and Urlaub, 1980, Proc. Natl. Acad. Sci. 77:44216). Two approaches have been taken in order to obtain cells that express either MTX resistance or dCF resistance associated with VWF expression. Then either cell line can be subsequently used to fuse to other cells that express factor VIII:c with the ability to select for either MTX or dCF resistance.

MTX Amplification in CHO DHFR deficient Cells

Plasmid pMT2VWF and pAdD26SVpa(3) were mixed 10:1 and transfected by $CaPO_4$ coprecipitation into CHO DUKX-B11 cells as described by Kaufman and Sharp (1982, J. Mol. Biol. 150:601). Cells were selected for the DHFR positive phenotype by growth in the absence of nucleosides and colonies pooled and selected for increasing MTX resistance. The results indicated that VWF expression increased with increasing MTX resistance and are depicted in the Table below:

| MTX Amplification of VWF Expression in CHO Cells | |
|---|---|
| CHO Selection | ng/ml VWF |
| 0.02 uM MTX | — |
| 0.2 uM MTX | 56 |
| 1.0 uM MTX | 91 |
| 5.0 uM MTX | 278 | dCF Selection for VWF in CHO DHFR Deficient Cells

The plasmid pMT2ADA-VWF was introduced into CHO DUKX-B11 cells as described in Example VIII and cells selected for growth in ADA selective alpha media with 4 uM xyl-A, 0.03 uM dCF, 10 ug/ml hypoxanthine, 10 ug/ml thymidine, and 10 ug/ml of penicillin and streptomycin. One clone PM5F was derived which expressed 3-5 pg of VWF/cell/day. This clone was subsequently used for fusion to factor VIII:c cell lines and as a recipient for the introduction of factor VIII:c genes.

Fusion of Factor VIII:c and VWF Expressing Cell Lines

The factor VIII:c expression plasmid pLA2 has been described (Toole et al., 1986, Proc. natl. Acad.; International Application No. PCT/US86/00774). This plasmid has been introduced into DUKX-B11 CHO cells by protoplast fusion with selection for DHFR from the 3' region of the factor VIII-DHFR transcript (See PCT/US86/00774). A cell line was derived by selection for MTX resistance to 1.0 uM MTX and has been named LA3-5. This cell line expresses a deleted form of Factor VIII:c at 3-5 uUnits/cell/day (in 10% fetal calf serum). This modified factor VIII:c also binds and requires VWF for efficient synthesis. LA3-5 was fused to PM5F and hybrids were selected that expressed both the MTX resistance and dCF resistance phenotypes.

For fusion, PM5F was treated with diethylepyrocarbonate (0.03% for 30 minutes on ice) in order to kill the PM5F. These cells were then fused by polyethylene glycol induced cell fusion to LA3-5. For fusion, DEPC treated pMSF cells were centrifuged onto LA 3-5 ($1.5 \times 10^6$ cells) at 2000 rpm for 8 minutes in an IEC model K centrifuge. After centrifugation, supernatant was removed and 2 ml of 50% PEG solution was added. PEG was left on for 45 seconds & cells were washed thoroughly with serum free medium Cells were left plated with medium containing serum for 48 hrs. & were then subcultured into selective medium containing 4 uM xyl-A, 0.03 uMdCF, in the presence of 10 ug/ml of each of the following: thymidine, hypoxanthinine, streptomycin, and penicillin. However, it was not necessary to include the thymidine and hypoxanthine. A pool of hybrids was obtained which expressed 0.73 pg/cell/day of VWF and 0.2-2.0 units/ml/day of factor VIII:c. The pool was subsequently grown in the absence of thymidine and hypoxanthine in the presence of 0.5 uM MTX. These cells were cloned in alpha media with 4 uM xyl-A, 0.03 uM dCF, and 0.5 uM MTX to obtain the following clones:

| Factor VIII;c and VWF Coexpression in CHO Cells | | |
|---|---|---|
| Clone | VWF Expression pg/cell | Factor VIII:c Expression uUnits/Cell-media |
| E6 | 16 | 2.8 - defined |
| | | 3.8 - 10% FCS |
| B9 | 20 | 4.5 - defined |
| | | 5.1 - 10% FCS |
| H6 | 34 | 7.7 - defined |
| | | 8.7 - 10% FCS |
| B1 | 8.1 | 10.5 defined |
| | | 11.8 10% FCS |

These results demonstrate the ability of the VWF and Factor VIII:c co-expressing cell lines to produce high levels of factor VIII:c in defined media.

EXAMPLE X

Introduction of Factor VIII:c Genes into Cells Expressing VWF

A factor VIII:c deletion mutant of 907 amino acids has been constructed by heteroduplex mutagenesis (PCT/US86/00774) which directly fuses the 90 kDa cleavage site (at residue 740) to the 76 kDa cleavage site (at 1647). The resultant plasmid p90-76R has the factor VIII:c coding region 5' on the polycistronic transcription unit in pMT2. Protoplasts of E. coli HB101 harboring this plasmid were prepared and fused to the VWF expressing cell line PM5F as described in Example VIII. 48 hrs after recovery from protoplast fusion, the cells were subcultured into DHFR selection media (alpha media lacking nucleosides with 10% dialyzed fetal calf serum, 4 uM xyl-A, and 0.03 uM dCF. After two weeks, transformants were isolated and assayed for Factor VIII:c expression. Approximately 20% of the transformants which had arisen expressed both VWF and Factor VIII:c. Results for one transformant are indicated below:

| Cell Line | Factor VIII:c Activity | |
|---|---|---|
| F1 | 1.5 uUnits/cell | 1375 mUnits/ml def. media |
| | 0.95 uUnits/cell | 1330 mUnits/ml 10% FCS |

(with VWF = 1.69 ug/ml 1.85 pg/cell)

These results demonstrate the ability to select for the DHFR phenotype in the PM5F cell line and to coexpress factor VIII:c and the VWF in order to alleviate the serum dependence for factor VIII:c expression.

What is claimed is:

1. A method of producing Factor VIII:c protein in a serum free medium comprising the steps of:
   (1) transfecting mammalian cells with (a) an expression vector containing a gene encoding a Factor VIII:c protein and (b) an expression vector containing a gene encoding VWF, both of said genes being in operative association with an expression control sequence therefor, said transfected mammalian cells being capable of expressing said Factor VIII:c protein and said vWF;
   (2) applying both of said genes;
   (3) culturing said transferred mammalian cells in a serum-free culture medium under suitable culture conditions; and
   (4) recovering said Factor VIII:c protein associated with said vWF from said culture medium.

2. The method of claim 1 comprising the additional step of separating said Factor VIII:c protein from said VWF.

3. A method of claim 1, wherein said transferred mammalian cells are CHO cells.

4. A method of producing Factor VIII:c-like protein exhibiting procoagulant activity and which is encoded for by DNA sequences capable of hybridizing to DNA coding for Factor VIII:c in a serum-free medium comprising the steps of:
   (1) transfecting mammalian cells with (a) an expression vector containing a gene encoding a Factor VIII:c-like protein and (b) an expression vector containing a gene encoding vWF, both of said genes being in operative association with an expression control sequence therefor, said transfected mammalian cells being capable of expressing said factor VIII:c-like protein and said vWF;
   (2) amplifying both of said genes;
   (3) culturing said transfected mammalian cells in a serum-free culture medium under suitable culture conditions; and
   (4) recovering said Factor VIII:c-like protein associated with said VWF from said culture medium.

5. The method of claim 4 comprising the additional step of separating said Factor VIII:c-like protein from said VWF.

6. The method of claim 4 wherein said transfected mammalian cells are CHO cells.

* * * * *

UNITED STATES PATENT AND TRADEMARK OFFICE
CERTIFICATE OF CORRECTION

PATENT NO. : 5,198,349
DATED : March 30, 1993
INVENTOR(S) : Kaufman and Adamson

It is certified that error appears in the above-identified patent and that said Letters Patent is hereby corrected as shown below:

Col. 2, line 4, please replace "ellicit" with --elicit--.

Col. 3, line 11, please replace "phopholipids" with --phospholipids--.

Col. 4, line 43, please replace "rFIII" with --rFVIII--.

Col. 4, line 44, please replace "gycol" with --glycol--.

Col. 13, line 52, please replace "Factor VII:c" with --Factor VIII:C--.

Col. 15, line 52, please replace "Proc. natl. Acad." with --Proc. Natl. Acad. Sci--.

Col. 17, line 12, please replace "applying" with --amplifying--.

Col. 4, line 43, after "phospholipid" insert --.--

Signed and Sealed this

Twelfth Day of April, 1994

Attest:

BRUCE LEHMAN

*Commissioner of Patents and Trademarks*

*Attesting Officer*

UNITED STATES PATENT AND TRADEMARK OFFICE
CERTIFICATE OF CORRECTION

PATENT NO. : 5,198,349

DATED : March 30, 1993

INVENTOR(S) : Kaufman

It is certified that error appears in the above-identified patent and that said Letters Patent is hereby corrected as shown below:

Column 17:
In claim 1, line 12, please replace "transferred" with --transfected--.

Signed and Sealed this

Thirtieth Day of May, 1995

Attest:

BRUCE LEHMAN

*Attesting Officer*     *Commissioner of Patents and Trademarks*